(12) United States Patent
Jongen et al.

(10) Patent No.: US 7,860,216 B2
(45) Date of Patent: Dec. 28, 2010

(54) DEVICE AND METHOD FOR POSITIONING A TARGET VOLUME IN RADIATION THERAPY APPARATUS

(75) Inventors: Yves Jongen, Louvain-la-Neuve (BE); Rudi Labarbe, Boncelles (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 12/096,990

(22) PCT Filed: Dec. 12, 2006

(86) PCT No.: PCT/BE2006/000133
§ 371 (c)(1),
(2), (4) Date: Oct. 27, 2008

(87) PCT Pub. No.: WO2007/068066
PCT Pub. Date: Jun. 21, 2007

(65) Prior Publication Data
US 2009/0168960 A1 Jul. 2, 2009

(30) Foreign Application Priority Data
Dec. 12, 2005 (EP) .................................. 05447279

(51) Int. Cl.
*G01K 5/08* (2006.01)
(52) U.S. Cl. ........................ 378/68; 378/205
(58) Field of Classification Search ............ 378/64–65, 378/205, 208, 209, 195, 196, 197, 198
See application file for complete search history.

(56) References Cited

U.S. PATENT DOCUMENTS

| 5,117,829 A | 6/1992 | Miller et al. |
| 6,865,253 B2 | 3/2005 | Blumhofer et al. |
| 2003/0206614 A1 | 11/2003 | Kendrick et al. |
| 2005/0109939 A1* | 5/2005 | Engler et al. ............. 250/336.1 |

FOREIGN PATENT DOCUMENTS

| DE | 101 39 934 A1 | 3/2003 |
| WO | 03/024333 A1 | 3/2003 |
| WO | 2005/053794 A1 | 6/2005 |

* cited by examiner

*Primary Examiner*—Hoon Song
(74) *Attorney, Agent, or Firm*—Fitch, Even, Tabin & Flannery

(57) ABSTRACT

Device for positioning a target volume (112) such, as a phantom or a patient in a radiation therapy apparatus, said apparatus directing a radiation beam (405) towards said target (112), characterized in that it comprises:—a target support (100) whereon the target is immobilized; a two dimensional radiation detector (103) fixed with fixations means (101, 102, 104, 106 107; 301, 302, 304, 305, 306; 208, 209) in a known geometric relationship to said target support (100), said radiation detector (103) being capable of detecting the position of intersection of said radiation beam (105) with said detector (103); correcting means for correcting the relative position of said beam (105) and said target support 100), based on said detected intersection position.

11 Claims, 4 Drawing Sheets

DEVICE AND METHOD FOR POSITIONING A TARGET VOLUME IN RADIATION THERAPY APPARATUS

TECHNICAL FIELD

The invention relates to the field radiation therapy. More particularly, the invention relates to a device and method for positioning a target volume in a radiation therapy apparatus. Said target can be a patient or a phantom representing said patient for irradiation tests.

DESCRIPTION OF RELATED ART

When a tumour has been discovered in a patient's body, the tumour first needs to be visualized for further diagnostic. This can for example be performed with an imaging system such as a computed tomography (CT) scanning system or an MRI apparatus. A 3D representation of the tumour volume is obtained. With the information collected in this way a clinical treatment plan can be generated. Then the actual treatment with a radiation therapy apparatus can start.

In a known hadron therapy apparatus, like e.g. used in proton therapy, the therapeutic radiation beam, accelerated by an accelerator such as a cyclotron, is guided to the therapy room, where the patient is fixed to a therapy table such as a therapy couch. Prior to irradiation, the therapy table must be positioned accurately by means of a positioning system, such that the affected part of the patient's body is in alignment with the therapeutic radiation beam.

Often irradiation is performed from a variety of different angles. A gantry system is then used to rotate the radiation source. For hadron therapy, typically, the hadronic particle beam, e.g. a proton, a neutron, an alpha particle or a carbon ion beam, is emitted out of a nozzle towards a particular target region of the patient, e.g. a tumour to be treated. Tumour location are determined in an imaging system (CT-scan or MRI), together with/through markers. These markers may be natural bony landmarks, visible in the diagnostic imaging system, or artificial markers, such as gold seeds inserted (under the skin) in the patient, or marks made on the skin with a radioopaque ink, in case of CT-scan imaging. It is a requirement that all these types of markers are visible under both the diagnostic imaging system used and the system used for positioning the patient in the radiation therapy apparatus.

In a gantry radiation therapy apparatus, the isocentre is defined as the point where the axis of the nozzle beam path intersects the gantry axis of rotation. The isocentre remains fixed throughout the treatment process.

It is required that the patient be accurately positioned with respect to radiation therapy apparatus, so that the beam only irradiates the target as designed in the treatment planning. Otherwise, the beam could damage healthy cells within the patient's body. So, the precision of the patient positioning before treatment is highly critical to a successful operation.

Typically, the patient undergoing the therapy receives periodic treatments wherein the target is irradiated repeatedly over the course of an extended period of time. Therefore, before each treatment session, a proper positioning of the patient is required.

As already mentioned, the process of identifying the precise location of the target volume immediately prior to a dose of therapeutic radiation is of key importance. To ensure that the patient is accurately positioned with respect to the therapy device, the position of the target is initially determined with respect to one or more monuments within the body of the patient. This operation is performed in an outside diagnostic imaging system, such as a PET-scanner. In standard patient positioning, the monuments are comprised of points on the bones structure of the patient and the location of the target is then determined with respect to these monuments. The patient is then located on the couch of a patient positioner in the therapy device. The patient positioner is moved to the so-called 'set-up position', where the patient position is determined through the use of radiographs, laser-lights and/or other localization aids having the capability to locate said monuments. A correction is determined as required. The patient positioner is then used to move the patient to the successive treatment positions. In the set-up position, the patient is located at or near the isocentre. In this approach it is assumed that the tumour never moves between the time of the CT scan and all the treatment days.

PRIOR ART DISCUSSION

U.S. Pat. No. 5,117,829 discloses a patient alignment system and procedure for radiation treatment.

The method disclosed therein comprises the steps of obtaining a 3D image of the region to be treated, together with monuments;

compute from said 3D image a digitally reconstructed radiograph (DRR) representing the image that would be obtained from said region to be treated and monuments from an imaging system located in the therapy device;

obtain a digital radiograph (DR), including location of monuments;

compare location of monuments on DRR and DR, and compute a correction for the position of the patient from this comparison.

The DR may be obtained in from an anterior/posterior (AP) or lateral direction, for different types of corrections. In the case of an AP image, a X-ray source must be inserted into the nozzle, for directing an imaging beam along the direction of the treatment beam, and removed before treatment beam delivery. This method however, assumes that the relative geometry of the imaging device or devices in the therapy device with respect to the treatment beam as delivered is known in a reliable way. In this and similar patient positioning methods, a precise and repeatable mechanical patient positioner is required, having means for correcting as well translational as angular coordinates.

Many of the known methods for patient positioning in a radiation therapy apparatus have been designed with the application to a gantry radiation treatment apparatus in mind. An example of such a method and device is the above discussed U.S. Pat. No. 5,117,829. In this document, a target isocenter location is selected and marked that identifies the particular location within the treatment volume at which the treatment beam should be directed. The radiation therapy apparatus isocenter is that point 90 in the center of the gantry at which the beams converge regardless of the position around the circumference of the gantry from which the beams originate. It is thus the purpose of the treatment plan to bring the tissue volume of interest, i.e., the target isocenter, to a particular point in space having a fixed geometrical relationship relative to the radiation therapy apparatus isocenter 90. Typically, for many treatment plans, the target isocenter will be brought directly to the radiation therapy apparatus isocenter 90. However, radiation therapy devices with a radically different principle have also been designed. Patent document WO 2005/053794 describes such a design, where a so-called "excentric" gantry carries a beam away from a rotation axis of said gantry towards two or more distinct treatment rooms. Thanks to an appropriate shielding design, a patient may be treated in one of these treatment rooms while another patient is being prepared in another such treatment room. The concept of isocenter is absent in such a device.

There is therefore a need for a device and method for positioning a patient in a radiation therapy apparatus providing an improved accuracy and reliability, that must be applicable in a device lacking an isocenter.

SUMMARY OF THE INVENTION

The present invention overcomes the shortcomings of the conventional art and may achieve other advantages not contemplated by conventional devices.

According to a first aspect of the invention, a device for positioning a target such as a phantom or a patient, in particular the tumour of a patient to be treated, in a radiation therapy apparatus, said apparatus directing a radiation beam towards said target, is disclosed. Said device advantageously comprises:

a target support whereon the target is immobilized;

a two dimensional radiation detector fixed with fixation means in a known geometric relationship to said target support, said radiation detector being capable of detecting the position of intersection of said radiation beam with said detector;

correcting means for correcting the relative position of said beam and said target support, based on said detected intersection position.

The device comprises a first set of ionization chambers in a first orientation and a second set of ionization chambers in a second orientation, thereby allowing determination of intersection point. A matrix device can also be used.

The fixation means can be fixation frames affixed to the target support, e.g. in indexed fixed holes, whereby said detector may be located in close proximity to the target. By having the detector located close to the target and in particular a tumour in the patient, a positioning precision as high as the resolution in the detector may be obtained.

The fixation means can also comprise fixation frames affixed to target support with a slidable carriage sliding on rails whereby said detector may located in close proximity to the target and in particular the tumour in the patient, in a continuous manner.

The fixation frames may be are circular arcs or polygons.

Preferably, the radiation detector and radiation beam are arranged such that said radiation beam intersects said detector in a substantially perpendicular direction, thereby providing a good precision in the intersection point.

The correcting means may comprise means for applying a precise correction displacement to said radiation beam. This solution is especially preferred in radiation therapy apparatuses having scanning magnets for moving the beam. A correction offset is then simply applied to the scanning magnets. The correcting means may also comprise means for applying a precise correction displacement to the target support. Said detectors are positioned in front of the target.

According to a second aspect of the invention, a method is provided for positioning a target in a radiation therapy apparatus comprising the steps of:

determining a relative position of the target and a radiation detector;

providing means ensuring that said relative position remains fixed in the subsequent steps;

determining the intended intersection point of the radiation beam with detector;

directing a sub-therapeutic radiation beam towards detector device and determining the actual intersection point of said beam with said detector;

computing a correction vector being the difference between the two locations;

applying a correction to the relative position between radiation beam (105) and radiation detector (103), whereby the actual intersection point coincides with said intended intersection point. Said target can be a phantom for irradiation tests or a tumour in a patient.

The application of a correction to the relative position between radiation beam and radiation detector preferably comprises the step of moving the radiation beam. Alternatively, the application of a correction to the relative position between radiation beam and radiation detector comprises the step moving together the target and the detector.

Preferably, the step of determining relative position of target and detector comprises the step providing a detector having three or more points for fixation to a target support, said points having a known geometric relationship with said detector;

installing the target in a fixed way on target support;

providing markers on said target support at the fixation points of said detector, said markers being visible in an imaging modality;

obtaining an image of said target using an imaging modality where both said target and said markers are visible;

determining from said image the geometric relationship of said target and said markers;

inferring therefrom the geometric relationship between said target and said detector.

According to a third aspect of the invention, the use of the device and/or the method according to the invention in a radiation therapy apparatus having an excentric gantry.

Other aspects and advantages of embodiments of the invention will be discussed with reference to the figures and to the detailed description of preferred embodiments.

DETAILED DESCRIPTION OF SEVERAL EMBODIMENTS OF THE PRESENT INVENTION

Figure 1:
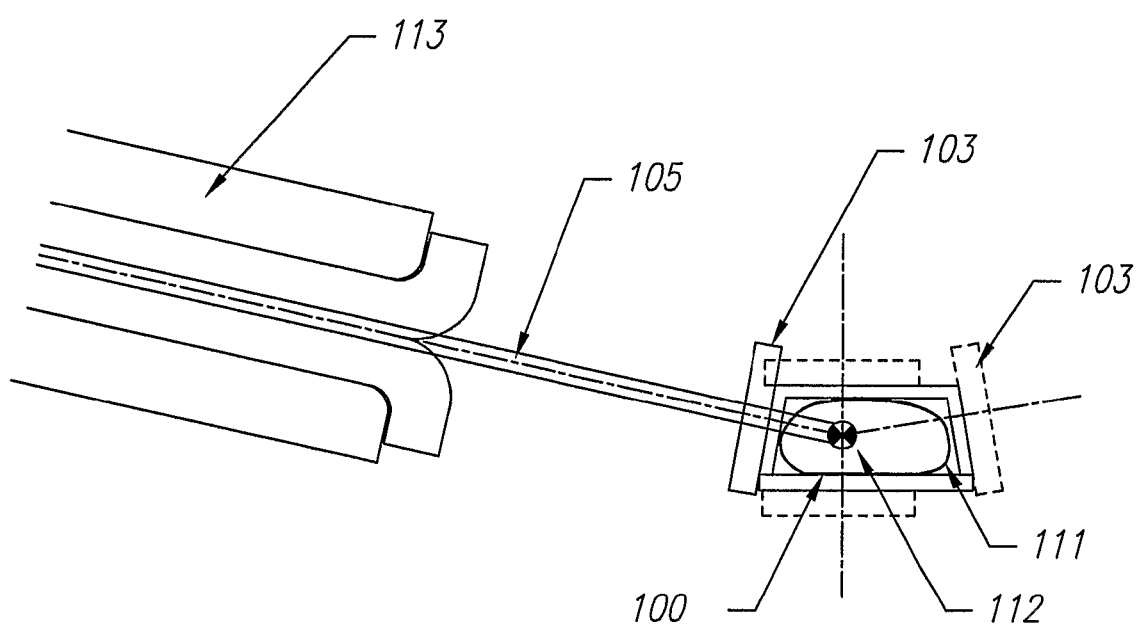
FIG. 1 is a schematic view of a radiation therapy apparatus using a device according to the invention.

FIG. 1 is a partial view of a radiation therapy apparatus where a device according to the invention is used. A radiation beam 105 is directed towards a patient 111 lying on a patient support 100. The irradiation nozzle is shown symbolically as a deflecting magnet 113. According to the invention, a radiation detector 103, shown in sectional view on FIG. 1, is fixed to patient support 110 closely located to the patient 111 and its tumour 112, in such a way that beam 105 intersects detector 103 under a substantially perpendicular direction.

Figure 2:
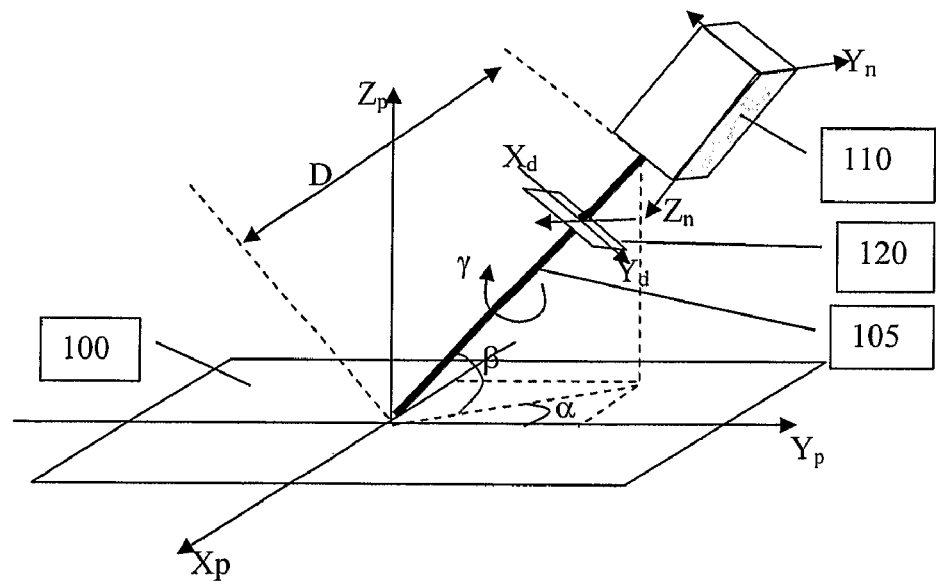
FIG. 2 represents a definition of the target support coordinate system and of the nozzle coordinate system.

Referring to FIG. 2, the general geometric framework for discussing patient positioning in a radiation therapy apparatus is described. A patient (not represented) is lying on a couch 100 or other patient support. The patient coordinate system (Xp, Yp, Zp) has its origin at a reference point in the tumour. The Yp axis is parallel to the long axis of the couch 100. The Xp axis is parallel to the short axis of the couch 100. The Zp axis is vertical. The treatment beam 105 is delivered by a nozzle 110. A coordinate system (Xn, Yn, Zn) is attached to the nozzle. The axis Zn is collinear with the treatment beam. The axis Xn and Yn define the orientation of the aperture placed on the nozzle.

The position of the treatment beam 105 is determined by the following conditions:
1. The treatment beam 105 must intersect the centre of the patient coordinate system (as the reference point in the tumour is at the centre of the patient coordinate system)
2. The distance D between the origin of the patient coordinate system and the nozzle is defined by the Treatment Planning System. It is not critical that this distance is measured accurately. Indeed, the range of the particles in the patient is related to the thickness of the tissues. If the distance D is too large (or too short), this implies that the air gap between the patient and the nozzle is too large (too short, respectively). The thickness of tissues remains unchanged. Therefore, increasing (decreasing, respectively) the air gap will not have a significant effect on the range of the particles in the patient.
3. The elevation angle $\beta$ between the treatment beam and the (Xp, Yp) plane is defined by the Treatment Planning Software (TPS). This angle is related to the gantry angle.
4. The horizontal rotation angle $\alpha$ between the Yp axis and the projection of the treatment beam in the (Xp, Yp) plane is defined by the TPS. This angle is related to the couch rotation angle.
5. The rotation of the (Xn, Yn) coordinate system around the radiation beam is defined by the angle $\gamma$ that is computed by the TPS. This angle defines the rotation of the beam aperture with respect to the patient. For symmetrical beams, this angle is not important.

In conclusion, six parameters are required to specify the relative position of the Patient Coordinate System (Xp, Yp, Zp) and of the Nozzle Coordinate System (Xn, Yn, Zn):
   Three coordinates defining the position of the origin of the patient coordinate system in the nozzle coordinate system. These coordinates are defined by conditions (1) and (2)
   Three angles ($\alpha, \beta, \gamma$) defining the relative orientation of the patient coordinate system and of the nozzle coordinate system. These angles are defined by conditions (3), (4) and (5).

The relative position and orientation of the patient and nozzle has been defined by 6 parameters expressed in the coordinate systems defined in FIG. 2. It is obvious that other coordinate systems can also be used. For example, instead of using the angles ($\alpha, \beta, \gamma$) as defined in FIG. 2, one could define the rotation, pitch and roll angle of the couch. However, whatever coordinate system is used, one will always need to define three angles and three position coordinates. A transformation can be used to convert from one coordinate system to another. Therefore, we will base our discussion on the coordinate systems presented in FIG. 2 without loss of generality.

In the positioning devices and methods known in the art, an imaging system, comprising an imaging beam source and an imaging beam receiver having a known geometric relationship with respect to the nozzle coordinate system is directed at the patient. Said imaging system identifies the location of visible landmarks which have known geometric relationships with respect to the tumour reference point. From the difference between the expected location of these landmarks and the detected locations, a correction vector is computed.

In the framework of the invention, we introduce a new coordinate system. Let us suppose that a measurement plane 120 is placed in the treatment beam 105. The beam profile is measured in this plane. Ideally, this plane is perpendicular to the treatment beam. The measurement plane defines two coordinate axes: Xd, Yd. Three angles ($\alpha d, \beta d, \gamma d$) define the relative orientation of the measurement plane coordinate system with the nozzle coordinate system.

During the treatment, the angular orientation ($\alpha, \beta, \gamma$) of the patient with respect to the nozzle is set by selecting the proper couch rotation angle, couch pitch and roll angles and gantry rotation angle. The correct angular orientation of the couch and gantry rotation obtained through the knowledge of the geometry of the treatment room environment. These positions may in addition be checked using known technologies (for example, using stereo cameras to check the position of markers on the nozzle and on the patient or on the couch, such as described, e.g. in document US 2002/0065461).

Once the angular orientation of the patient has been checked, the translational position of the patient must be verified. As previously mentioned, the position along one of the translation direction (the Zn axis) is not critical. The present invention describes a method to check the relative position of the patient and of the treatment beam along the two remaining translation directions: the Xn and Yn axis.

Figure 3:
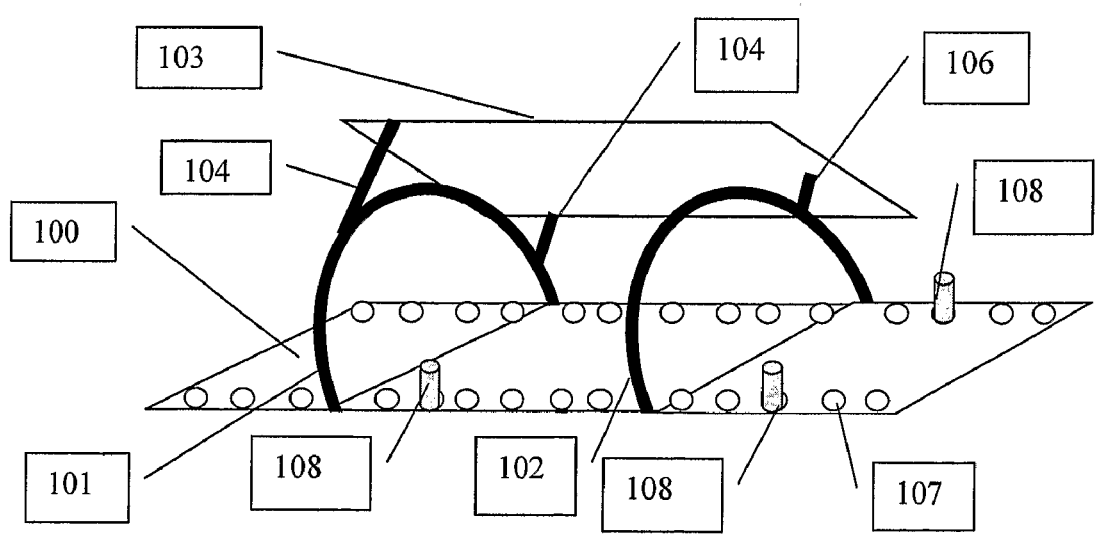
FIGS. 3, 4 and 5 represent features of a couch according to respectively, a first, a second and a third embodiment of the invention.

The patient will be lying on the couch 100 (see FIG. 3). Two series of fixation holes 107 are provided on the couch 100. These holes are indexed and are used to attach a patient immobilization device to the couch 100. This provides a good reproducibility for positioning the patient on the couch 100. A plane radiation detector 103 determines the spatial distribution in two dimensions of the intensity of the radiation beam 105. The radiation detector is able to measure the intensity distribution in two dimensions in a plane substantially perpendicular to the axis of the radiation beam 105. This radiation detector may be a set of two strip ionizations chambers, with a first strip ionization chamber in one orientation and a second ionization chamber in another orientation. The radiation detector 103 may also be a pixel ionization chamber. Other types of radiation detectors may be used, such as semiconductor or film. A selection of a radiation-transparent radiation detector is preferred because a such radiation detector may be left in place during the treatment. The value of the angle between the plane of the radiation detector 103 and the radiation beam is known.

At least 3 position markers 108 are installed on the couch 100 or on the patient. The position markers 108 are manufactured with a material that is visible both in a CT scanner and with a patient alignment system installed in the treatment room (e.g. stereovision infra-red camera or an X-ray imaging system). These markers are known in the art from e.g. U.S. Pat. No. 6,865,253.

Figure 6:
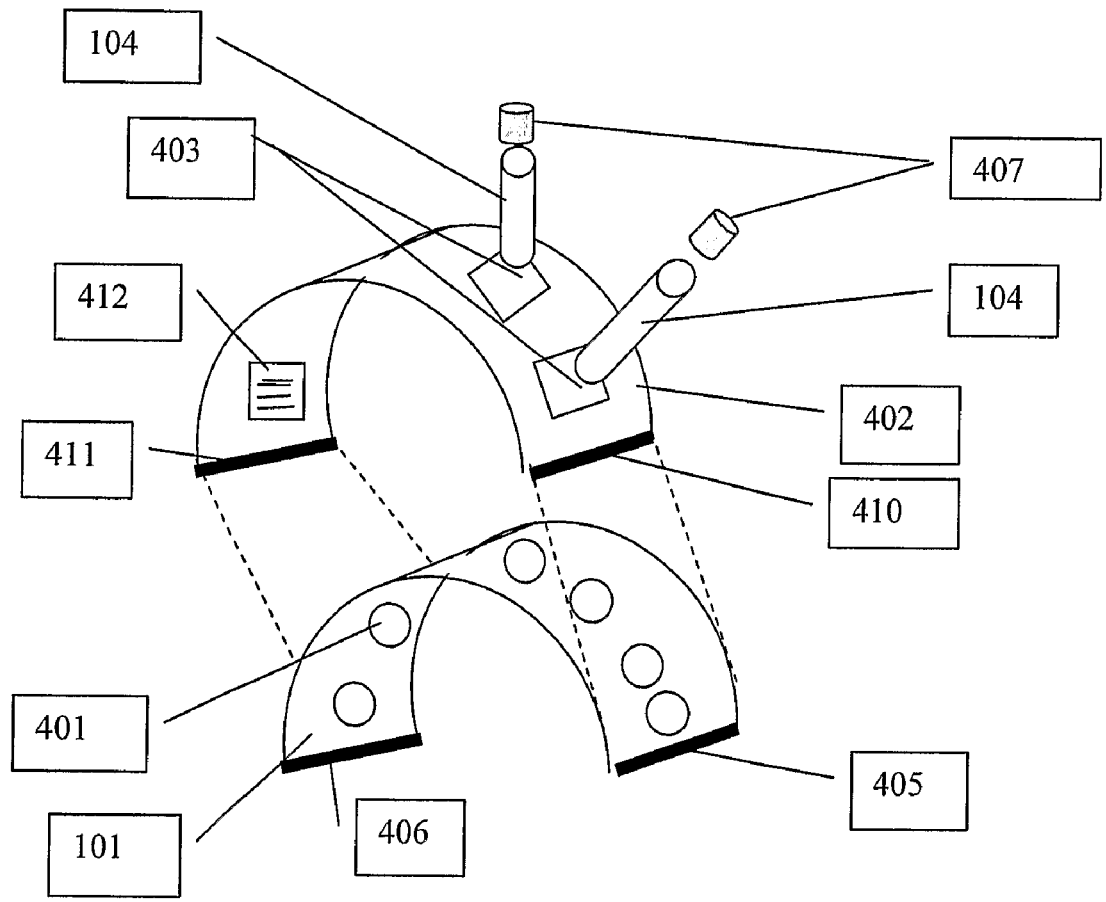
FIG. 6 is a schematic view of circular fixation frames.

Two frames are attached to the couch. Several types of frames assembly are possible: in a first embodiment, the frames are shaped as half circles (FIG. 3). The two frames 101 and 102 are fixed to the couch 100 using the fixation holes 107. The fixation holes 107 used to attach the frames 101 and 102 are selected so that the distance between the approximate position of tumour in the patient and the first frame 101 is substantially equal to the distance between the tumour and the second fixation frame 102. Therefore, the tumour is approximately in the middle between the two fixation frames. The half circle frames can be attached to the top of the couch if the particle beam is coming from above the couch. Alternatively, they can be fixed to the bottom of the couch if the particle beam comes from under the couch. FIG. 3 represents only the configuration when the proton beam is coming from above the couch. There are fixation holes 401 equidistantly drilled on the rim of the circular fixation frame 101 and 102 (see FIG. 6). These fixation holes are indexed. The three fixation legs 104, and 106 are inserted in the fixation holes 401. The radiation detector 103 is inserted on the fixation legs. The three fixation holes 401 and the length of the fixation legs 104 and 106 are chosen so that the radiation detector 103 is measuring the radiation field in a plane that is substantially perpendicular to the radiation beam. The fixation legs will be specific for a patient. A mechanism is implemented in order to make sure that the correct fixation holes 401 are used (FIG. 6). A plastic strip 402 is placed on the rim of the fixation frame 101 or 102. There are two holes 403 drilled in the plastic strip 402. There is one hole drilled on the plastic strip that will cover the fixation frame 102. The plastic strip will cover all the holes 401 of the rims, except those that will be used to fix the legs 104 and 106 of the radiation detector 103. The plastic strip 402 is equipped with two fixation systems 410 and 411 that will attach the plastic strip to the fixation points 405 and 406 on the rim of the fixation frames 101 and 102. The fixations systems 410 and 411 are asymmetrical, so that there is only one possible position in which to place the plastic strip 402 on the rims. The fixation systems used on frames 101 and 102 will be different from the fixation system used on frame 102 in order to avoid inverting the plastic strips of these two frames. The position of the holes 403 is carefully determined so that the measurement plane radiation detector will be positioned substantially perpendicular to the radiation beam. The position of the hole will therefore be different for each patient. A label 412 is placed on the plastic strip 402 in order to uniquely link the plastic strip and the patient. The label could, for example, be a bar code. The fixation legs 104 or 106 are inserted in the holes 401. The markers 407 are placed at the end of the legs 104 and 106. These markers simulate the position of the radiation detector. The markers can be visualized in a CT-scanner. The circular shape of the fixation frame 101 and 102 and the equidistance between the fixation holes 401 allows the fixation of the radiation detector 103 in a large range of angles around the patient. The angular range is covered by discrete angle steps.

Figure 4:
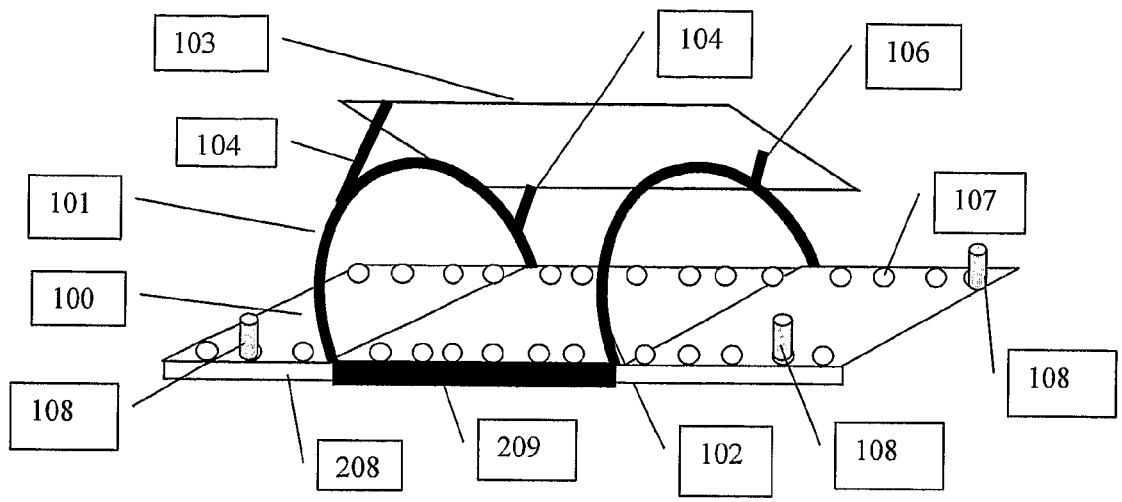

In a second embodiment, the frames are shaped as half circles (FIG. 4). Two rails 208 are located on both sides of the couch 100. The two half circle frames 101 and 102 are attached to a carriage 209 that slides on the rail 208. The position of the carriage on the rail is indexed so that it is possible to reproducibly move the half circle frame to a specified position. The carriage is moved so that the tumour is approximately located in middle between the two fixation frames 101 and 102. The radiation detector is fixed to the frames 101 and 102 as described in Embodiment 1. The plastic strips 402 are used as described in Embodiment 1.

Figure 5:
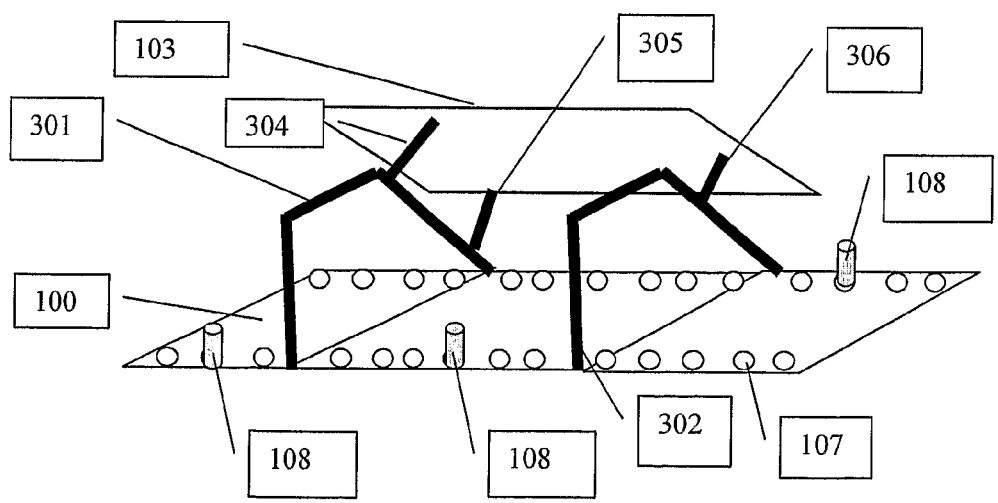

In a third embodiment, the frames have a non circular shape, for example they can have a trapezoidal shape (FIG. 5). The two trapezoidal frames 301 and 302 are fixed to the couch 100 using the fixation holes 107. There are two fixation holes on each side of the trapezoidal fixation frame 301. There is one fixation hole on each side of the trapezoidal frame 302. The legs 304, 305 and 306 of the radiation detector 103 are inserted in the fixation holes. In this embodiment, the radiation detector can be at three different positions around the patient.

The method of patient positioning comprises two steps: a first step of calibration of the radiation detector prior to the treatment, and a second step of actually positioning the patient during treatment The first step, calibration of the radiation detector, is described hereafter: When a new radiation detector is used, it must be calibrated. Indeed, the radiation detector measures the distribution of the radiation intensity in the measurement plane. The intensity distribution is described within the coordinate system of the radiation detector (Xd, Yd in FIG. 2). The position of the origin and the orientation of the axis of this coordinate system will be different for each radiation detector. Furthermore, the relative position of the origin of the coordinate system and of the markers 407 will be different for each detector. In addition, the orientation of the coordinate axis of the radiation detector 403 with respect to the position marker 407 will be different for every radiation detector. The calibration consists in finding the position of the origin of the radiation detector coordinate system with respect to the markers 407. It also consists in finding the orientation of the axis of the radiation detector coordinate system with respect to the markers 407. This calibration process is done using known procedures. This calibration must be done for every new radiation detector.

The second step, of actually positioning the patient comprises the following steps:

1. a CT scan of the patient is acquired in a CT scanner;
2. using a Treatment Planning Software, the operator identifies the position of the tumour, determines the incidence angles of the treatment beams and prepares the treatment plan;
3. when the incidence angles of the different treatment beams are known, the operator determines which treatment room of the excentric gantry will be used for each treatment beam. She also determines optimum position of the radiation detector 103 on the fixation frames 101 and 102, which fixation holes 401 of the fixation frame 101 and 102 will be used and the optimum length of the fixation legs 104 and 106. The parameters are selected so that the measurement plane of the radiation detector is substantially perpendicular to the treatment beam. The plastic strips 402 are prepared with the holes 403 drilled at the correct position.
4. On the treatment day, the patient lies on the couch 101. The operator places the fixation device on the patient in order to install the patient at approximately the correct position on the couch. The operator installs the fixation frames 101 and 102 on the couch. The operator installs the plastic strips 402 for this patient. The operator installs the fixation legs 104 and 106 on the fixation frames. The operator places the markers 407 on the fixation legs.
5. A CT scan or a CBCT scan of the patient, of the marker 108 and the markers 407 is acquired. Using positioning software, the operator determines the relative position of the tumour and the position of the markers 407. The operator also determines the orientation of the patient coordinate system with respect to the markers 108 and the position of the tumour with respect to the markers 108.
6. Based on the position of the markers 407 and the calibration procedure described above, the software determines the position and orientation of the detector coordinate system with respect to the patient coordinate system. Based on the knowledge of the incidence angle of the treatment beam in the patient coordinate system, the position of the tumour and the position of the measurement plane, the software determines the point of intersection of the radiation beam with the measurement plane. The theoretical coordinate of the intersection point 501, expressed in the radiation detector coordinate system, is where the centre of the radiation beam must be directed.

7. The patient remains immobile on the couch. The couch is moved from the CT scanner to the treatment machine. The patient is placed in front of the nozzle delivering the treatment beam so that the tumour is approximately placed on the axis of the radiation beam.
8. The angular orientation of the patient with respect to the treatment beam is verified by measuring the position of the markers 108 using known technologies (e.g. stereo-vision infra-red camera). The patient angular orientation is adjusted by varying the pitch, roll and rotation angle of the couch until the measured angular orientation of the markers 108 is correct. The patient angular orientation is now correct.
9. The operator must now adjust the relative translation position of the patient and the beam along the Xn and Yn axis of FIG. 2. The theoretical coordinates of the intersection point of the treatment beam with the radiation detector plane 103 has been computed at step 6. A particle beam 500 with sub-therapeutic intensity is aimed at the patient, along a trajectory identical to that that will be used by the therapeutic beam. The beam intensity is low enough not to cause any damage to the patient while being high enough to be detectable by the radiation detector 103. The relative translation position of the patient and the treatment beam is adjusted using the sub-therapeutic beam 500 using one of the following method:
   a. The couch is moved along an axis parallel to the (Xn,Yn) plane until the sub-therapeutic beam 500 intersects the detector plane at the theoretical position 501. This is the preferred alignment method for the double scattering mode.
   b. The sub-therapeutic beam is shifted transversally in the (Xn,Yn) plane until it intersects the detector plane at the theoretical position 501. A DC voltage is applied to the beam scanning magnets in order to shift the sub-therapeutic beam. This is the preferred method for uniform scanning and pencil beam scanning.

All these steps are performed either by a technical operator or by a computer through a specialized software calculator under the control of a technical operator.

Finally, only when all these steps are performed, a final step, e.g. irradiating the patient, which is a therapeutic step and which is not part of the present method, is performed.

In case of irradiation tests, a phantom is submitted to the irradiation beam. In case of therapeutic treatment, only once the patient position and the sub-therapeutic beam position have been adjusted as described in step 9, the same settings are used for the treatment beam. Only this last step is made under the control of a doctor.

Finally, it should be noted that the detectors are preferably positioned in front of the patient or of the phantom. This means that during the treatment of the patient through the irradiation beam, these detectors must be either transparent or removed from their position.

By using the device and method of the invention, an improved accuracy in the positioning of a patient with respect to a therapeutic beam is obtained. This device and method is particularly, but not exclusively, suited for use in a radiation therapy device having an excentric gantry. The radiation detector being close to the patient skin, the error in positioning of patient with respect to the beam can be as small as the resolution of the radiation detector. By using the variation of the method and device where the position correction is applied by applying an offset to the beam, the complexity and cost of a precise and patient positioner may be avoided. The nominal position of the patient support is not a critical factor in the solution of the invention. Moreover, in the framework of the invention, one determines the position of the actual beam with respect to the patient, and not of the beam delivery device. One is thereby relieved from any errors in the alignment of the treatment beam with respect to the nozzle.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

DRAWING ELEMENTS LIST

100 target support (couch)
101 fixation frame (half circle)
102 fixation frame
103 radiation detector
104 fixation leg
106 fixation leg
105 treatment beam
107 fixation holes
108 position markers
110 nozzle
111 patient
112 target (tumour or phantom)
113 gantry magnets
120 measurement plane
301 trapezoidal frame
302 trapezoidal frame
304 leg
305 leg
306 leg
208 two rails on both sides of couch
209 carriage
401 fixation holes
402 plastic strips
403 radiation detector
403 holes
405 fixation point
406 fixation point
407 markers
410 fixation system
411 fixation system
412 label
500 sub-therapeutic particle beam
501 intersection point

The invention claimed is:

1. A device for positioning a target in a patient in a radiation therapy apparatus, the apparatus directing a radiation beam towards the target, the device comprising:
   a target support for immobilizing the target;
   a two-dimensional radiation detector fixed with fixation device in a predetermined geometric relationship to the target support, the two-dimensional radiation detector configured to detect an intersection position of the radiation beam with the detector; and
   correcting device configured to correct a relative position of the beam and the target support, based on the detected intersection position;
   wherein the fixation device comprises fixation frames affixed to the target support, the two-dimensional radiation detector located in close proximity to the target.

2. The device according to claim 1, wherein the fixation device comprises fixation frames affixed to the target support with a slidable carriage sliding on rails, the two-dimensional radiation detector located in close proximity to the target.

3. The device according to claim 1, wherein the fixation frames are circular arcs.

4. The device according to claim 1, wherein the two-dimensional radiation detector and the radiation beam are arranged such that the radiation beam intersects with the two-dimensional radiation detector in a substantially perpendicular direction.

5. The device according to claim 1, wherein the correcting device comprises an application device configured to apply a precise correction displacement to the radiation beam.

6. The device according to claim 1, wherein the correcting device comprises an application device configured to apply a precise correction displacement to the target support.

7. The device according to claim 1, wherein the target support comprises indexed fixed holes for affixing the fixation frames.

8. The device according to claim 1, wherein the fixation frames are polygons.

9. A method for positioning a target in a patient in a radiation therapy apparatus, comprising:
  determining a relative position between the target and a two-dimensional radiation detector;
  providing a fixation device configured to fix the relative position during the subsequent steps;
  determining an intended intersection point of the radiation beam with the two-dimensional radiation detector;
  directing a sub-therapeutic radiation beam towards the two-dimensional radiation detector and determining an actual intersection point of the beam with the two-dimensional radiation detector;
  computing a correction vector which is a difference between locations of the intended and the actual intersection points; and
  applying a correction to a relative position between the radiation beam and the two-dimensional radiation detector, whereby the actual intersection point coincides with the intended intersection point;
  wherein determining the relative position of the target and the two-dimensional radiation detector comprises:
  providing a two-dimensional radiation detector having three or more points for fixation to a target support, the points having a geometric relationship with the two-dimensional radiation detector;
  installing the target in a fixed way on a target support;
  providing markers on the target support at fixation points of the two-dimensional radiation detector, the markers being visible in an imaging modality;
  obtaining an image of the target using an imaging modality where both the target and the markers are visible;
  determining from the image the geometric relationship of the target and the markers; and
  inferring therefrom the geometric relationship between the target and the two-dimensional radiation detector.

10. The method according to claim 9, wherein applying a correction comprises moving the radiation beam to correct the relative position between the radiation beam and the two-dimensional radiation detector.

11. The method according to claim 9, wherein applying a correction comprises moving the target and the two-dimensional radiation detector to correct the relative position between the radiation beam and the two-dimensional radiation detector.

* * * * *